US005147313A

United States Patent [19]
Dikeman

[11] Patent Number: 5,147,313
[45] Date of Patent: Sep. 15, 1992

[54] MEDICAL FLUID DELIVERY SYSTEM WITH UNIQUELY CONFIGURED PUMP UNIT AND FLUID DELIVERY SET

[75] Inventor: Cary Dikeman, Leawood, Kans.

[73] Assignee: Entracare Corporation, St. Louis, Mo.

[21] Appl. No.: 601,191

[22] Filed: Oct. 22, 1990

[51] Int. Cl.[5] .............................................. A61M 1/00
[52] U.S. Cl. ........................... 604/153; 128/DIG. 12; 417/423.14; 417/476
[58] Field of Search ............... 604/151, 152, 153, 131, 604/132, 118, 119, 120, 121, 122, 253; 128/DIG. 12, DIG. 13; 417/423.14, 476, 477

[56] References Cited

U.S. PATENT DOCUMENTS

| 293,130 | 12/1987 | Ashie et al. | D24/53 |
|---|---|---|---|
| 3,731,679 | 5/1973 | Wilhelmson | 604/152 |
| 3,993,066 | 11/1976 | Virag | 128/214 |
| 4,013,072 | 3/1977 | Jess | 128/214 |
| 4,397,648 | 8/1983 | Knute | 604/253 |
| 4,515,535 | 5/1985 | D'Silva | 604/153 |
| 4,548,600 | 10/1985 | Ruschke | 604/122 |
| 4,592,741 | 6/1986 | Vincent | 604/118 |
| 4,629,448 | 12/1986 | Carlsson et al. | 604/153 |
| 4,798,580 | 1/1989 | Demeo et al. | 417/476 |
| 4,913,703 | 4/1990 | Pasqualuvi et al. | 604/153 |

FOREIGN PATENT DOCUMENTS 9007947  7/1990  World Int. Prop. O. .......... 604/153

Primary Examiner—Gene Mancene
Assistant Examiner—Michael Lynch
Attorney, Agent, or Firm—Senniger, Powers, Leavitt & Roedel

[57] ABSTRACT

A medical fluid delivery system comprising a peristaltic pump unit and a fluid delivery set adapted to be operatively mounted on the pump unit. The fluid delivery set comprises a drip container for holding fluid to be pumped by the pump unit, and a formation on the drip container having an external contour of unique configuration. The pump unit comprising a holder having a socket therein for receiving and holding the drip container in an operative position on the pump unit. The socket has a uniquely configured internal contour adapted to mate with the uniquely configured external contour of the formation on the drip container whereby a fluid delivery set without the uniquely configured formation cannot be mounted in operative position on the pump unit.

22 Claims, 3 Drawing Sheets

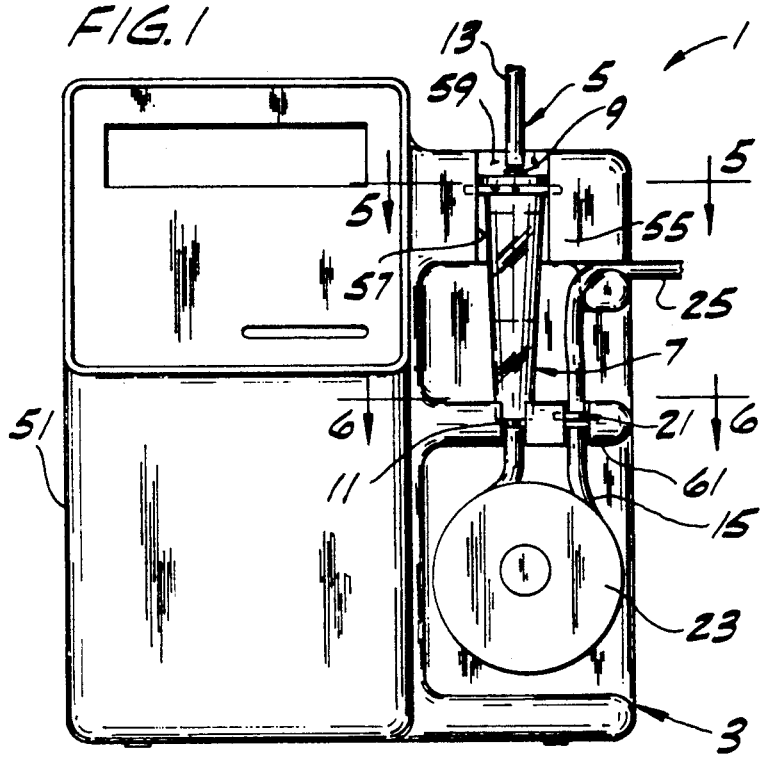
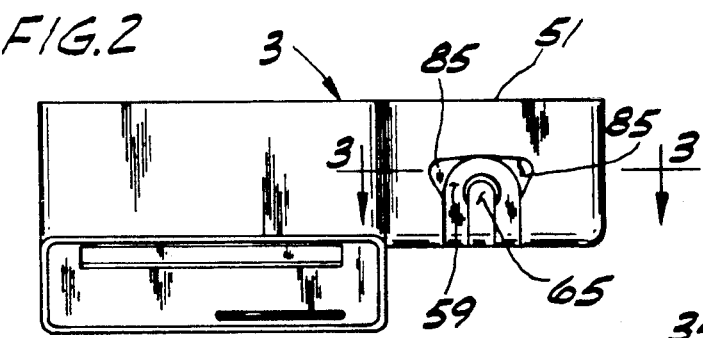
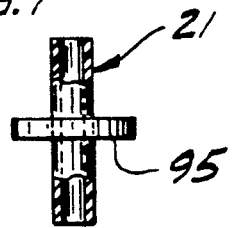
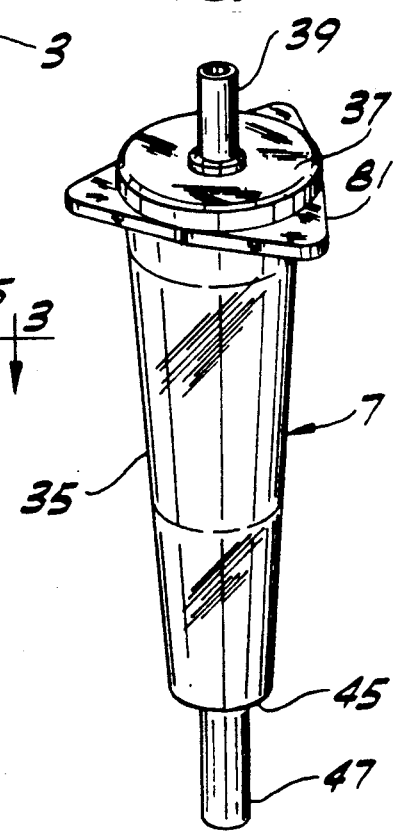

MEDICAL FLUID DELIVERY SYSTEM WITH UNIQUELY CONFIGURED PUMP UNIT AND FLUID DELIVERY SET

BACKGROUND OF THE INVENTION

This invention relates to fluid delivery systems for providing perenteral nutrition, enteral nutrition or other fluids to patients who require infusion of fluids, and particularly to such systems which use disposable fluid delivery sets in conjunction with a pump unit (usually a peristaltic pump and motor unit) for supplying such fluids to patients at a controlled delivery rate.

Disposable fluid delivery sets typically comprise a drip container (sometimes referred to in the trade as a "drip chamber") adapted to be mounted in fixed position on a pump and motor unit, an outlet tube which is connected to the outlet of the drip container and which is adapted to extend around a rotor of the pump and motor unit, and a mounting piece at the end of the outlet tube which is held in fixed position on the pump and motor unit for connection of the outlet end of the outlet tube to a patient infusion system. The arrangement is such that, as the rotor is driven, fluid is peristaltically pumped from the drip container to the patient infusion system. A medical fluid delivery system of this type is described in U.S. Pat. No. 4,913,703.

Disposable fluid delivery sets are made by numerous different manufacturers, as are peristaltic pump units. These sets and units are often perceived as being interchangeable, so that the user of a pump unit made by a particular manufacturer may use disposable fluid delivery sets from one or more different manufacturers. This may lead to problems if the fluid delivery set is not compatible with the peristaltic pump unit.

SUMMARY OF THE INVENTION

Among the several objects of this invention may be noted the provision of a medical fluid delivery system comprising a peristaltic pump unit which is designed to operate only if a particular type of fluid delivery set is used; the provision of such a system which provides for safe and reliable delivery of fluid to a patient; and the provision of such a system which is economical to manufacture.

Generally, the present invention is directed to a medical fluid delivery system comprising a peristaltic pump unit and a fluid delivery set adapted to be operatively mounted on the pump unit. The fluid delivery set comprises a drip container for holding fluid to be pumped by the pump unit, and a formation on the drip container having an external contour of unique configuration. The pump unit comprises a holder having a socket for receiving and holding the drip container in an operative position on the pump unit. The socket has a uniquely configured internal contour adapted to mate with the uniquely configured external contour of the formation on the drip container whereby a fluid delivery set without the uniquely configured formation cannot be mounted in operative position on the pump unit.

The present invention is also directed to a pump unit having the uniquely configured socket described above.

Other objects and features will in part apparent and in part pointed out hereinafter.

BRIEF DESCRIPTION OF THE DRAWINGS

FIG. 1 is a front elevation of a medical fluid delivery system of the present invention comprising a peristaltic pump and motor unit and a fluid delivery set mounted on the pump and motor unit;

FIG. 2 is a top plan view of the pump and motor unit of FIG. 1;

FIG. 4 is a perspective view of a drip container of the fluid delivery set;

FIG. 7 is an elevational view of a mounting piece of the fluid delivery set.

Corresponding parts are designated by corresponding reference numerals in the drawings.

DETAILED DESCRIPTION OF THE PREFERRED EMBODIMENT

Figure 3:
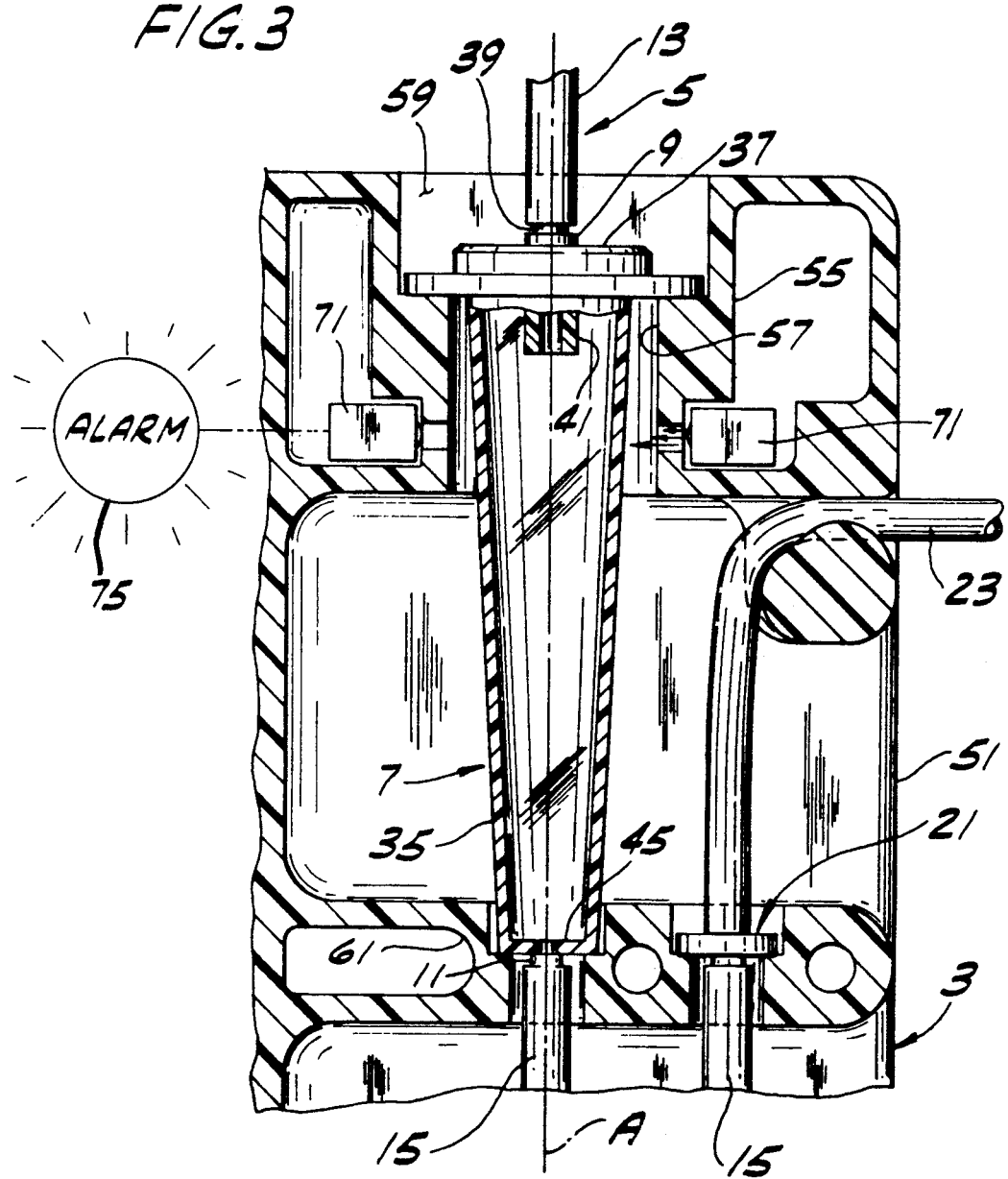
FIG. 3 is an enlarged vertical section on line 3—3 of FIG. 2.
Figure 6:
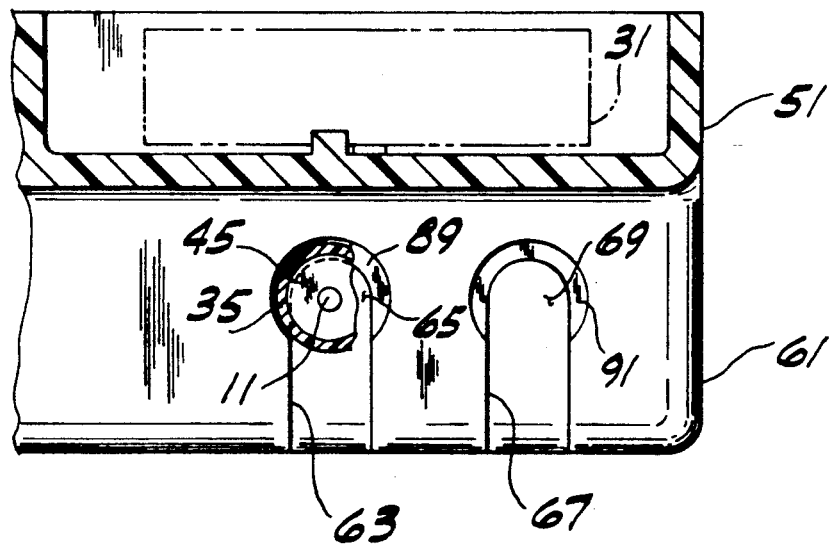
FIG. 6 is an enlarged horizontal section on line 6—6 of FIG. 1.

Referring now to the drawings, and first more particularly to FIGS. 1-3, a medical fluid delivery system is designated in its entirety by the reference numeral 1. The system is shown as comprising a peristaltic pump unit, generally indicated at 3, and a fluid delivery set generally indicated at 5. The fluid delivery set includes a drip container (sometimes referred to in the trade as a "drip chamber"), generally designated 7, adapted to be mounted on the pump unit and having an inlet 9 and an outlet 11 at its upper and lower ends, respectively, an inlet tube 13 connected to a source of medical fluid (not shown) for delivery of fluid to the inlet 9 of the drip container, and an outlet tube 15 connected at one end to the outlet 11 of the drip container and at its other end to one end of a tubular mounting piece 21 adapted to be held in fixed position on the pump unit 3. The arrangement is such that the outlet tube 15 extends around a rotor 23 of the unit for engagement by the rotor to form a peristaltic pump of the type well known in the industry. A fluid delivery tube 25 is connected to the other end of the tubular mounting piece 21 (its upper end as illustrated) for delivery of fluid, such as enteral nutrition fluid, to a patient infusion system (not shown). The rotor 23 of the peristaltic pump is driven at various speeds by a suitable motor 31 in the housing (FIG. 6) to control the rate of delivery of fluid to the patient. It will be understood that this invention also has application to other types of pump units used in connection with various types of medical fluids, such as intravenous fluids or blood. In some systems, the motor 31 of the peristaltic pump unit may be replaced by gravity flow control apparatus.

As best illustrated in FIGS. 3 and 4, the drip container 7 comprises an elongate hollow member 35 tapering from its upper end to its lower end, and a cap 37 rigidly affixed (e.g., thermally welded) to the member at its upper end. The cap is formed with an integral tubular inlet fitting 39 extending upwardly from the cap, and an integral tubular cannula 41 extending downwardly from the cap into the interior of the hollow member. The inlet fitting 39 and cannula 41 are disposed on the central vertical axis A of the drip container and form the inlet 9 to the container, the inlet tube 13 being slidably fitted on the inlet fitting 39 of the cap 37 as shown in FIG. 2. The cannula 41 is of conventional design for providing a metered supply of fluid to the drip container. The hollow member 35 has a bottom wall 45 with an integral tubular outlet fitting 47 depending therefrom generally on the central vertical axis A of the container. This fitting 47 forms the outlet 11 of the container for slidable connection to the outlet tube 15.

The pump unit 3 comprises a housing 51, which may be of one-piece molded plastic construction, and means integrally formed with the housing for holding the drip container in an operative position on the unit. This holding means comprises an upper holding structure 55 at the front of the housing having a recess or notch 57 therein extending rearwardly from the front face of the structure. The upper portion of this recess 57 is enlarged to form an upper socket 59 for receiving and holding the upper end of the drip container 7. A shelf-like lower holding structure 61 is spaced below the upper holding structure 55 and above the rotor 23. This lower structure has a first recess or notch 63 therein extending rearwardly from the front edge of the structure. The upper portion of this recess 63 is enlarged to form a first lower socket 65 for receiving and holding the lower end of the drip container. The lower holding structure 61 also has a second recess notch or 67 therein spaced laterally from the first lower recess 63 and extending rearwardly from the front edge of the shelf. The upper portion of this second recess 67 is enlarged to form a second lower socket 69 for receiving and holding the aforementioned mounting piece 21 in fixed position, as will appear. The upper and lower holding structures 55, 61 are illustrated as being integrally formed with the housing 51, but this is not essential to the practice of this invention.

The pump unit 3 further comprises a conventional 2-part flow detector 71 immediately below the upper socket 59 at opposite sides of the recess 57 in the upper holding structure 55, the detector 71 being so positioned that when the drip container 7 is held in proper operative position by the upper and lower holding structures 55, 61, the detector is adapted to detect the rate of fluid as it drips from the cannula 41 and to signal an alarm 75 if the rate varies from a predetermined rate. It will be understood that the drip container must be precisely positioned in the upper and lower sockets 59, 65, as in FIG. 3, for the proper functioning of the detector; otherwise the alarm 75 will be signalled. The alarm may be any suitable type of alarm, such as a flashing light on the pump unit. In addition to signalling an alarm if the proper flow rate is not detected, the detector 71 may also signal the motor 31 of the pump unit 3 to shut off, so that the pump unit cannot be operated until the container 7 is properly seated in the upper socket. This ensures proper operation of the system for the precise rate of feed to the patient infusion system.

Figure 5:
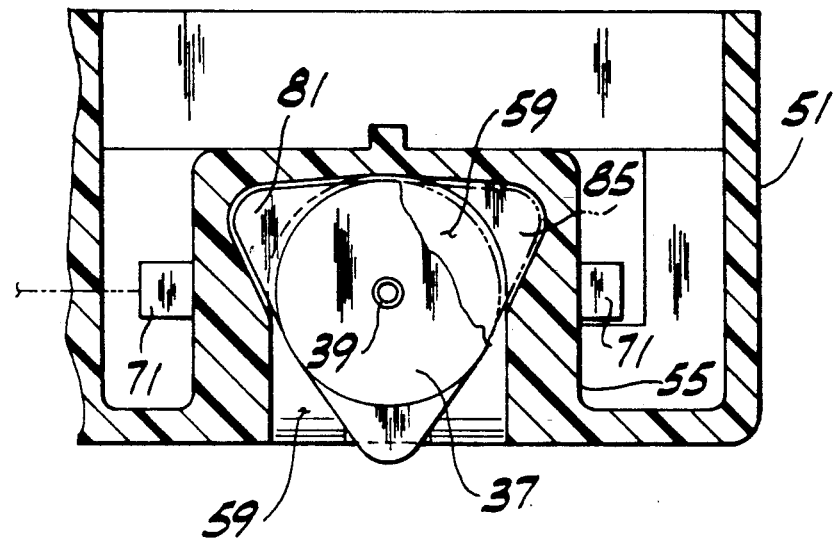
FIG. 5 is an enlarged horizontal section on line 5—5 of FIG. 1.

The present invention is concerned with assuring that a pump unit 3 designed in accordance with this invention can be used only with a fluid delivery set 5 compatible with the pump unit. To accomplish this, the drip container 7 has a uniquely configured formation thereon. More specifically, the cap 37 of the drip container is formed with an integral flange 81 (which may be referred to generally as flange means) projecting laterally with respect to the drip container adjacent its upper end in a plane generally at right angles to the central longitudinal (vertical) axis A of the container. This flange has an external contour of unique (i.e., special, unusual) configuration. As illustrated in FIG. 4, this configuration is triangular. Also in accordance with this invention, the upper socket 59 of the pump unit has a uniquely configured internal contour adapted to mate with the external contour of the flange. Thus, in the specific embodiment illustrated in the drawings, the socket 59 has a configuration suitable for mating with triangular flange 81 (see FIGS. 2 and 5). It will be understood, of course, that the unique mating configurations of the flange 81 and socket 59 may vary so long as they are especially adapted only for one another. For example, the flange and socket may have virtually any non-circular configuration, including various polygonal shapes, for example. Moreover, the drip container 7 may have other types of uniquely configured formations thereon. The type of formation and its precise location and configuration may vary; what is important is that the external configuration of the formation (e.g., 81) on the container and the internal configuration of the upper socket 59 should be uniquely configured to mate with one another so that a fluid delivery set 5 not uniquely configured to fit the pump unit cannot be used on the pump unit.

The upper socket 59 in the upper holding structure 55 is defined in part by upwardly facing first support surfaces or shoulders 85 engageable by the flange 81 on the drip container 7 for supporting the drip container in proper (operative) position relative to the flow detector 71. The shoulder configuration may vary depending on the shape of the flange 81 or other type of formation used. Similarly, the first lower socket 65 in the lower holding structure is defined in part by an upwardly facing second support surface or shoulder 89, generally part circular in shape, engageable by the bottom wall 45 of the drip container 7. It will be noted in this regard that the vertical distance between shoulders 85 and 89 should closely correspond to the vertical distance between the underside of the flange 81 and the underside of the bottom wall 45 of the container. The second lower socket 69 in the lower holding structure 61 is defined in part by an upwardly facing support surface or shoulder 91, also generally part circular in shape, engageable by a circular flange 95 extending around the tubular mounting piece 21 for supporting the mounting piece in proper position. Each of the three sockets 59, 65, 69 formed in the upper and lower holding structures 55, 61 are open at the front of the pump unit 3 to readily permit the drip container 7, outlet tube 15 and mounting piece 21 to be entered into respective sockets so that the fluid delivery set 5 may be properly mounted on the unit.

It will be observed from the foregoing that a pump unit 3 and fluid delivery set 5 of the present invention are uniquely compatible, so that a fluid delivery set without a drip container 7 having a uniquely configured formation (e.g., flange 81) cannot be mounted in an operative position on the pump unit and thus cannot be used with the pump unit. In the embodiment of the invention described above, the "operative" position is one where the drip container is properly positioned relative to the flow detector 71, but it will be understood that "operative" position should be construed broadly to mean any position where the drip container is mounted on the pump unit for proper operation of the system.

It will also be understood that the present invention is intended to cover any uniquely configured formation on the drip container which has an external contour compatible with a uniquely configured socket on the pump unit, the intended result being that drip containers without such a uniquely configured formation are "locked out" of the pump unit, much like a key which does not fit a lock.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A medical fluid delivery system comprising:
a peristaltic pump unit, and
a fluid delivery set adapted to be operatively mounted on the pump unit, said fluid delivery set comprising a drip container having a longitudinal axis for holding fluid to be pumped by the pump unit, and a formation on the drip container having an external contour of unique configuration, said external contour being non-circular in a plane generally transverse to said longitudinal axis of the drip container,
said pump unit comprising holding means having a socket for receiving and holding said drip container in an operative position on the pump unit,
said socket having a uniquely configured non-circular internal contour adapted to mate with the uniquely configured external contour of said formation on the drip container when the drip container is received in the socket whereby a fluid delivery set without said uniquely configured formation cannot be mounted in said operative position on the pump unit.

2. A medical fluid delivery system as set forth in claim 1 wherein said uniquely configured formation on the drip container comprises flange means projecting laterally from the drip container, said flange means having a non-circular external contour and said socket having a non-circular internal contour.

3. A medical fluid delivery system as set forth in claim 1 wherein said drip container comprises an elongated hollow member having upper and lower ends, an inlet at its upper end, and an outlet at its lower end, said uniquely configured formation comprising flange means projecting laterally with respect to the drip container adjacent its upper end in a plane generally at right angles to the central longitudinal axis of the drip container.

4. A medical fluid delivery system as set forth in claim 3 wherein said flange means has a non-circular external contour and said socket has a non-circular internal contour.

5. A medical fluid delivery system as set forth in claim 1 wherein said socket has an internal side wall of said unique configuration, and an upwardly facing support surface engageable by said uniquely configured formation of the drip container for supporting the drip container in said operative position.

6. A medical fluid delivery system as set forth in claim 5 wherein said uniquely configured formation comprises flange means projecting laterally from the drip container, said flange means having a non-circular external contour and said side wall of the socket having a non-circular internal contour.

7. A peristaltic pump unit as set forth in claim 1 wherein said pump unit comprises flow detector means positioned for detecting the rate of fluid flow into the drip container when the drip container is mounted in said operative position, and for signalling an alarm if the rate of flow is not at a predetermined rate, said flow detector means being so positioned relative to said socket that it is operable to signal said alarm if said uniquely configured formation of the drip container is not properly received in said socket.

8. A peristaltic pump unit as set forth in claim 7 wherein said flow detector means is positioned below said socket.

9. A medical fluid delivery system comprising:
a peristaltic pump unit, and
a fluid delivery set adapted to be operatively mounted on the pump unit, said fluid delivery set comprising a drip container for holding fluid to be pumped by the pump unit, and a formation on the drip container having an external contour of unique configuration,
said pump unit comprising holding means having a socket for receiving and holding said drip container in an operative position on the pump unit,
said socket having a uniquely configured internal contour adapted to mate with the uniquely configured external contour of said formation on the drip container whereby a fluid delivery set without said uniquely configured formation cannot be mounted in said operative position on the pump unit,
said uniquely configured formation on the drip container comprising flange means projecting laterally from the drip container, said flange means having a non-circular generally polygonal external contour and said socket having a non-circular generally polygonal internal contour.

10. A medical fluid delivery system as set forth in claim 9 wherein said flange means has a generally triangular external contour and said socket has a mating internal contour.

11. A medical fluid delivery system comprising:
a peristaltic pump unit, and
a fluid delivery set adapted to be operatively mounted on the pump unit, said fluid delivery set comprising a drip container for holding fluid to be pumped by the pump unit, and a formation on the drip container having an external contour of unique configuration,
said pump unit comprising holding means having a socket for receiving and holding said drip container in an operative position on the pump unit,
said socket having a uniquely configured internal contour adapted to mate with the uniquely configured external contour of said formation on the drip container whereby a fluid delivery set without said uniquely configured formation cannot be mounted in said operative position on the pump unit,
said drip container comprising an elongate hollow member having upper and lower ends, an inlet at its upper end, an outlet at its lower end and a central longitudinal axis, said uniquely configured formation comprising flange means projecting laterally with respect to the drip container adjacent its upper end in a plane generally at right angles to the central longitudinal axis of the drip container,
said flange means having a non-circular generally polygonal external contour and said socket having a non-circular generally polygonal internal contour.

12. A medical fluid delivery system as set forth in claim 11 wherein said flange means has a generally triangular external contour and said socket has a mating internal contour.

13. A medical fluid delivery system comprising:
a peristaltic pump unit, and
a fluid delivery set adapted to be operatively mounted on the pump unit, said fluid delivery set comprising a drip container for holding fluid to be pumped by the pump unit, and a formation on the drip container having an external contour of unique configuration,
said pump unit comprising holding means having a socket for receiving and holding said drip container in an operative position on the pump unit,
said socket having a uniquely configured internal contour adapted to mate with the uniquely configured external contour of said formation on the drip container whereby a fluid delivery set without said uniquely configured formation cannot be mounted in said operative position on the pump unit,
said socket having an internal side wall of said unique configuration, and an upwardly facing support surface engageable by said uniquely configured formation of the drip container for supporting the drip container in said operative position,
said uniquely configured formation comprising flange means projecting laterally from the drip container, said flange mean having a non-circular generally polygonal external contour and said side wall of the socket having a non-circular generally polygonal internal contour.

14. A medical fluid delivery system as set forth in claim 13 wherein said flange means has a generally triangular external contour and said side wall of the socket has a mating internal contour.

15. A medical fluid delivery system as set forth in claim 14 wherein said drip container comprises an elongate hollow member having upper and lower ends, an inlet at its upper end, an outlet at its lower end and a central longitudinal axis, said flange means projecting laterally with respect to the drip container adjacent its upper end in a plane generally at right angles to the central longitudinal axis of the drip container.

16. A medical fluid delivery system as set forth in claim 15 wherein said drip container has an upper end closed by a cap having said inlet therein, said flange means being integrally formed with said cap.

17. A peristaltic pump unit for use in a medical fluid delivery system, said pump unit being adapted for use with a fluid delivery set comprising a drip container for holding fluid to be pumped by the pump unit, said drip container having a longitudinal axis and a formation on the container with a uniquely configured, non-circular external contour, said pump unit comprising
a housing, and
means on the housing for holding said drip container in an operative position on the pump unit,
said holding means on the housing comprising a socket having an internal side wall with a uniquely configured, non-circular internal contour adapted to mate with the uniquely configured external contour of said formation on the drip container whereby a drip container without said uniquely configured formation cannot be mounted in operative position on said pump unit,
the internal side wall of the socket being generally polygonal in shape in a plane generally transverse to the longitudinal axis of the drip container.

18. A peristaltic pump unit as set forth in claim 17 wherein said socket has an upwardly facing support surface engageable by said uniquely configured formation on the drip container for supporting the drip container in said operative position.

19. A peristaltic pump unit as set forth in claim 17 wherein said pump unit comprises flow detector means positioned for detecting the rate o fluid flow into the drip container when the drip container is mounted in said operative position, and for signalling an alarm if the rate of flow is not at a predetermined rate, said flow detector means being so positioned relative to said socket that it is operable to signal said alarm if said uniquely configured formation of the drip container is not properly received in said socket.

20. A peristaltic pump unit as set forth in claim 19 wherein said flow detector means is positioned below said socket.

21. A peristaltic pump unit for use in a medical fluid delivery system, said pump unit being adapted for use with a fluid delivery set comprising a drip container for holding fluid to be pumped by the pump unit, said drip container having a formation thereon with a uniquely configured, non-circular, generally triangular external contour, said pump unit comprising:
a housing, and
means on the housing for holding said drip container in an operative position on the pump unit,
said holding means on the housing comprising a socket having an internal side wall with a uniquely configured, non-circular generally triangular internal contour adapted to mate with the uniquely configured generally triangular external contour of said formation on the drip container whereby a drip container without said uniquely configured formation cannot be mounted in operative position on said pump unit.

22. A peristaltic pump unit for use in a medical fluid delivery system, said pump unit being adapted for use with a fluid delivery set comprising a drip container for holding fluid to be pumped by the pump unit, said drip container having a formation thereon with a uniquely configured, non-circular external contour, said pump unit comprising:
a housing, and
means on the housing for holding said drip container in an operative position on the pump unit,
said holding means on the housing comprising a socket having an internal side wall with a uniquely configured, non-circular internal contour adapted to mate with the uniquely configured external contour of said formation on the drip container whereby a drip container without said uniquely configured formation cannot be mounted in operative position on said pump unit,
said holding means comprising an upper holding structure and a lower holding structure spaced below said upper holding structure, said socket, constituting an upper socket, being formed in said upper holding structure and being defined in part by an upwardly facing first support surface engageable by said uniquely configured formation of the drip container for supporting said drip container in said operative position, said lower holding structure having a lower socket for receiving and holding the bottom of said container, said socket being defined in part by an upwardly facing second support surface engageable by the bottom of the container when the drip container is in said operative position, the vertical spacing between said upwardly facing first and second support surfaces closely corresponding to the distance from the bottom of the container to said uniquely configured formation of the drip container.

* * * * *